(12) United States Patent
Brasfield et al.

(10) Patent No.: US 12,089,991 B2
(45) Date of Patent: Sep. 17, 2024

(54) ULTRASOUND TRANSMITTER WITH LOW DISTORTION AND CONCURRENT RECEIVE

(71) Applicant: Verasonics, Inc., Kirkland, WA (US)

(72) Inventors: Laurence C. Brasfield, Pittsburgh, PA (US); John A. Flynn, Seattle, WA (US); Ronald E. Daigle, Redmond, WA (US)

(73) Assignee: Verasonics, Inc., Kirkland, WA (US)

( * ) Notice: Subject to any disclaimer, the term of this patent is extended or adjusted under 35 U.S.C. 154(b) by 351 days.

(21) Appl. No.: 17/747,398

(22) Filed: May 18, 2022

(65) Prior Publication Data

US 2023/0371922 A1    Nov. 23, 2023

(51) Int. Cl.
| | |
|---|---|
| A61B 8/00 | (2006.01) |
| G01S 7/52 | (2006.01) |
| G01S 7/524 | (2006.01) |
| H02M 1/32 | (2007.01) |

(52) U.S. Cl.
CPC ............ *A61B 8/44* (2013.01); *G01S 7/52017* (2013.01); *G01S 7/5202* (2013.01); *G01S 7/524* (2013.01); *H02M 1/32* (2013.01); *G01S 7/5205* (2013.01)

(58) Field of Classification Search
CPC .... G01S 7/524; G01S 7/5202; G01S 7/52017; G01S 7/5205; A61B 8/44; A61B 8/58; H02M 1/32; H02M 7/5387
USPC ....................................................... 367/903
See application file for complete search history.

(56) References Cited

U.S. PATENT DOCUMENTS

| | | | | |
|---|---|---|---|---|
| 5,307,815 | A | * 5/1994 | Gatzke | .................... G01S 7/529 |
| | | | | 600/437 |
| 6,050,945 | A | * 4/2000 | Peterson | ................. G01S 7/526 |
| | | | | 600/443 |
| 6,241,676 | B1 | 6/2001 | Savord | |
| 6,584,861 | B1 | 7/2003 | Jespersen | |

(Continued)

FOREIGN PATENT DOCUMENTS

EP    2 711 093 A2    3/2014

OTHER PUBLICATIONS

Choi, H., et al., "Novel Power MOSFET-Based Expander for High Frequency Ultrasound Systems," *Ultrasonics* 54(1):121-130, Jan. 2014.

(Continued)

*Primary Examiner* — Daniel L Murphy
*Assistant Examiner* — Amie M Ndure
(74) *Attorney, Agent, or Firm* — Seed IP Law Group LLP

(57) ABSTRACT

An ultrasound transceiver that overcomes many of the deficiencies of conventional ultrasound transceivers by providing the ability to transmit high power and high frequency arbitrary waveforms with low distortion and with the ability to monitor the transmit signals through the receiver during the transmit period, the transceiver circuit having a transducer element to emit an ultrasound signal and to receive a reflected ultrasound signal, a transformer circuit having a transformer with a secondary winding coupled to the transducer element and a primary winding, an H-Bridge transmit waveform circuit coupled to the primary winding of the transformer to generate a transmit waveform signal to the transducer element via the transformer, an FET clamp coupled to the secondary winding of the transformer, and a receiver circuit having an input coupled to the FET clamp.

13 Claims, 4 Drawing Sheets

(56) References Cited

U.S. PATENT DOCUMENTS

| | | | |
|---|---|---|---|
| 6,759,888 B1 | 7/2004 | Wodnicki | |
| 6,891,311 B2* | 5/2005 | Phelps | G01S 7/5202 310/317 |
| 6,939,300 B2* | 9/2005 | Petersen | H04L 5/04 600/437 |
| 7,372,775 B2 | 5/2008 | Hayashi | |
| 7,901,358 B2 | 3/2011 | Mehi et al. | |
| 8,721,550 B2 | 5/2014 | Oguzman et al. | |
| 8,749,099 B2 | 6/2014 | Rossi et al. | |
| 9,772,645 B2 | 9/2017 | Rossi et al. | |
| 9,844,359 B2* | 12/2017 | Wegner | A61B 8/14 |
| 9,886,940 B2 | 2/2018 | Albertini et al. | |
| 9,958,538 B2 | 5/2018 | Richter et al. | |
| 10,873,328 B2 | 12/2020 | Ghisu et al. | |
| 2005/0243650 A1 | 11/2005 | Petersen et al. | |
| 2008/0262357 A1* | 10/2008 | Wodnicki | G01S 7/52017 600/459 |
| 2015/0087991 A1* | 3/2015 | Chen | G01S 7/52025 330/253 |
| 2016/0161603 A1* | 6/2016 | Flynn | G01S 7/5202 367/97 |
| 2022/0386997 A1* | 12/2022 | Igarashi | A61B 8/4444 |

OTHER PUBLICATIONS

Hsia, C., et al., "A Single-Chip High-Voltage Integrated Actuator for Biomedical Ultrasound Scanners," *Sensors* 19(5063), Nov. 2019, 21 pages.

Lufinka, O., "Ultrasonic Transceiver with the Possibilities of the Data Communication and the Two-Point Distance Measurement," 2016 International Conference on Applied Electronics (AE), Pilsen, Czech Republic, Sep. 2016, 4 pages.

Ricci, S., et al., "Linear Ultrasound Transmitter Based on Transformer with Improved Saturation Performance," *Electronics* 10(107), Jan. 2021, 15 pages.

Svilainis, L., et al., "Half Bridge Topology 500 V Pulser for Ultrasonic Transducer Excitation," *Ultrasonics*, Feb. 2015, 16 pages.

Svilainis, L. et al., "Investigation of the Half Bridge and Transformer Push-Pull Pulser Topologies for Ultrasonic Transducer Excitation," *Journal of Circuits, Systems, and Computers* 24(5), Jun. 2015, 14 pages.

Cho et al., "A micromachined silicon parallel acoustic delay line (PADL) array for real-time photoacoustic tomography (PAT)," SPIE BiOS, San Francisco, CA, USA, 2015, 6 pages.

* cited by examiner

ULTRASOUND TRANSMITTER WITH LOW DISTORTION AND CONCURRENT RECEIVE

BACKGROUND

Technical Field

The present disclosure is directed to ultrasound imaging and, more particularly, to transceivers for use with ultrasound transducers to transmit high power and high frequency arbitrary waveforms with low distortion, and with the ability to monitor the transmit signal through the receiver during the transmit period.

Description of the Related Art

Ultrasound systems typically utilize multi-element transducers to transmit ultrasound pulses into a medium and to receive echo signal returns the medium and from objects within the medium. Each transducer element can have its own independent transmitter and receiver, or transceiver, allowing for electronic focusing and steering of the ultrasound beam that is formed from a combination of transducer elements. To generate transmit pulses from the piezoelectric transducer elements of sufficient power, transmitters typically operate at peak-to-peak voltage levels of up to several 100 volts. In contrast, the received echo signal levels are significantly lower in signal strength than the transmit pulses, generally less than a few millivolts, which require a high gain receiver for adequate detection. Because of this large discrepancy between the transmit and receive signals, the receiver must be protected from a long recovery saturation or, at worse, from being damaged by a high transmit current.

Most ultrasound systems employ what is known as a Transmit/Receive (T/R) switch to protect the input of the receiver during the transmit period. A representative ultrasound transceiver circuit 10 is shown in FIG. 1, which includes a T/R switch 12 that is controlled by a control signal circuit 14. The T/R switch 12 is coupled to a transducer element 16 in response to the control signal circuit 14 switching the T/R switch 12 into an on condition during a transmit period. The on condition has the effect of implementing a low impedance path between a transmitter circuit 26 and the transducer element 16 and a high impedance path from the transmitter circuit 26 to a receiver circuit 20, which includes a variable gain amplifier 21 that has an input 34. Protection from a high voltage transmit waveform signal 22 transmitted from a transmit waveform signal generator 24 in the transmitter circuit 26 is provided for the receiver circuit 20 when the T/R switch 12 is in the on condition.

After the transmitter circuit 26 has completed sending the waveform signal 22, the T/R switch 12 is switched by the control signal 14 from a transmit state to a receive state 28 (shown by dashed lines in the T/R switch 12), which provides a low impedance path from the transducer element 16 to the receiver circuit 20 and further isolates the transmitter circuit 26 from attenuating or degrading the returning echo signals. The receiver circuit 20 may have other limiting circuits at its input, such as the resistive connection to ground 36 to protect against large receive signals, as well as a back-to-back diodes passive receiver protection circuit 30, and a capacitance 38 shown in FIG. 1.

The transceiver circuit of FIG. 1 has several issues that limit its effectiveness. Most ultrasound systems utilize a single T/R control signal 32 for all transceivers. In the case of a multi-element transducer, the transmit waveforms 22 may be emitted at various delay times to enable steering and focusing of the ultrasound beam in the medium (not shown). This generally requires a transmit period, where all transceivers stay in transmit mode until the last transmitter has transmitted. There is therefore a small region in the medium in front of the transducer where echos cannot be received during the transmit period. Likewise, it is not possible to transmit on an element or group of elements during the receive process without interrupting the entire set of receive signals. In addition, the T/R Switch 12, which is typically implemented with diodes and transistors, generally imparts some non-linear characteristics to the transmit waveform 22, producing some small distortion of the waveform shape. For example, a sine wave transmit waveform 22 may be distorted in a way that generates higher harmonics that could result in unwanted affects in the medium. Finally, the T/R Switch 12 generally limits the amount of electrical power that can be applied to the transducer 16 in transmit mode (the on condition) due to current limits and heating effects in the electronic switches.

BRIEF SUMMARY

The present disclosure is directed to ultrasound systems and methods, including an ultrasound transceiver, that overcome most of the deficiencies of conventional ultrasound transceivers by providing the ability to transmit high power and high frequency arbitrary waveforms with low distortion, and with the ability to monitor the transmit signals through the receiver during the transmit period.

In accordance with one aspect of the present disclosure, a circuit is provided that includes a transducer element structured to emit an ultrasound signal and to receive a reflected ultrasound signal, a transformer circuit coupled to the transducer element, the transformer circuit including a transformer having a primary winding and a secondary winding, the secondary winding coupled to the transducer element, a transmit waveform circuit coupled to the primary winding of the transformer and structured to generate a transmit waveform signal to the transducer element via the transformer circuit, and a receiver circuit having an input coupled to the secondary winding of the transformer and structured to be coupled to the transducer element.

In accordance with another aspect of the present disclosure, the transmit waveform circuit is an H-bridge circuit.

In accordance with a further aspect of the present disclosure, the circuit includes a clamp circuit coupled between the secondary winding of the transformer and the input of the receiver circuit. Preferably the clamp circuit includes an active clamp circuit having a pair of FET switches coupled in parallel to the input of the receiver circuit.

In accordance with yet a further aspect of the present disclosure, each of the FET switches in the pair of FET switches have a control terminal that is coupled to the transmit waveform generation circuit to receive an on-signal that is tied to a duration of transmit waveform signal.

In accordance with still yet another aspect of the present disclosure, an ultrasound device is provided that includes:
- a transducer circuit structured to transmit ultrasound signals and receiving corresponding echo signals and generating returning echo signals;
- a variable gain receiver having an input coupled to the transducer circuit;
- a transceiver capable of generating over 100 volts peak-to-peak waveforms across the transducer and receiving the returning echo signals from the transducer of less than one volt peak-to-peak, the transceiver including:

a transformer having a primary winding and a secondary winding, the primary winding coupled to the transducer;

a transmitter circuit coupled through the transformer to the transducer, the transmitter circuit comprising a transmit waveform generator structured to generate a transmit waveform, the transmit waveform generator coupled to the primary winding of the transformer so that the primary winding is driven by the transmit waveform generator, and the secondary is connected on one side to the transducer circuit and on another other side to the input of the variable gain receiver, with a maximum gain of at least 30 dB; and a protection circuit coupled between the secondary winding of the transformer and the input of the variable gain receiver and structured such that when the protection circuit is active it provides an impedance in the range of 0.1 to 1.0 ohms from the input of the variable gain receiver to ground during a transmit period of the transceiver so that the input of the variable gain receiver provides an effective ground for the transformer secondary winding during the transmit period; wherein the variable gain receiver can be active during the transmit period and can amplify a small voltage across the protection circuit to monitor the transmit waveform for amplitude and duration.

BRIEF DESCRIPTION OF THE SEVERAL VIEWS OF THE DRAWINGS

The foregoing and other features and advantages of the present disclosure will be more readily appreciated as the same become better understood from the following detailed description when taken in conjunction with the accompanying drawings, wherein.

DETAILED DESCRIPTION

Figure 1:
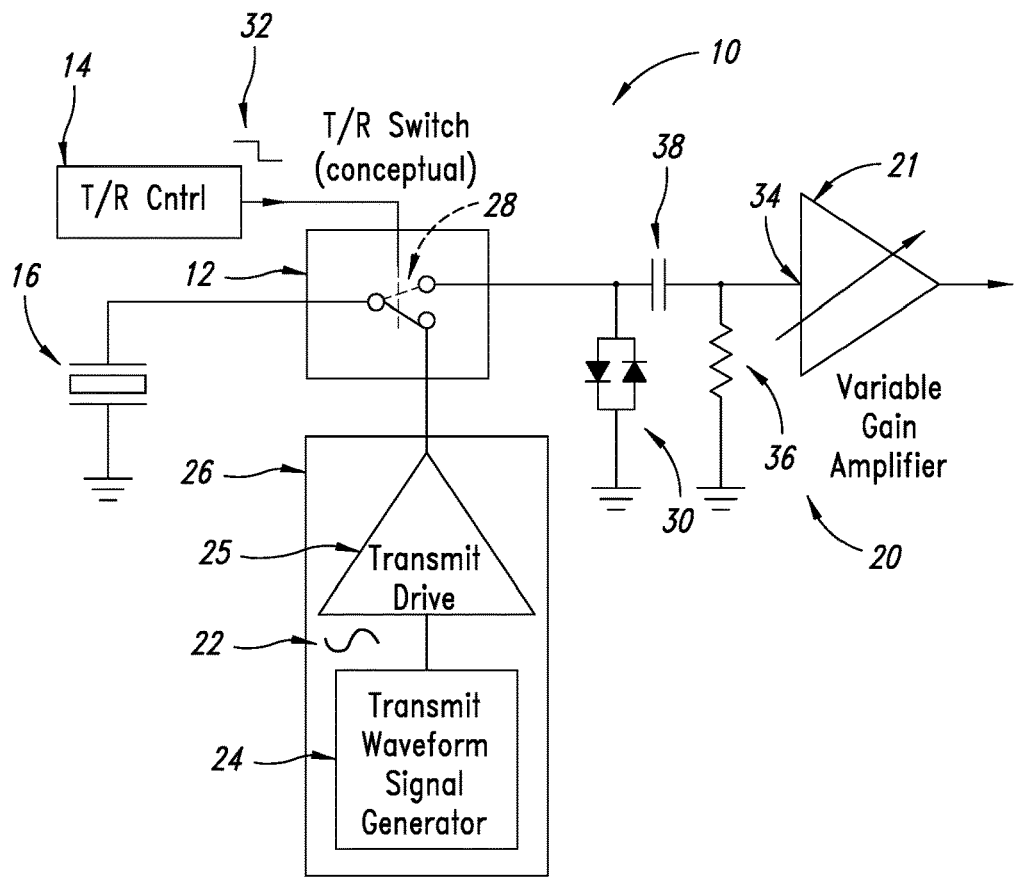
FIG. 1 is a schematic illustration of a conventional ultrasound transceiver with transmit/receive circuitry.

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, well-known structures associated with switches, transducers, amplifiers, control signal generators, programmable logic devices, memories, and transformers have not been shown or described in detail to avoid unnecessarily obscuring descriptions of the implementations.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one implementation" or "an implementation" means that a particular feature, structure or characteristic described in connection with the implementation is included in at least one implementation. Thus, the appearance of the phrases "in one implementation" or "in an implementation" in various places throughout this specification are not necessarily all referring to the same implementation. Furthermore, the particular features, structures, or characteristics may be combined in any suitable manner in one or more implementations. It will be appreciated that for simplicity and clarity of illustration, where considered appropriate, reference numerals may be repeated among the figures to indicate corresponding or analogous elements or steps.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

General Overview

Ultrasound systems typically utilize a transceiver connected to a transducer or transducer element to transmit ultrasound energy into a medium and receive echo signals returning to the transducer. The transceiver must be capable of producing high voltage signals to drive the transducer and able to receive the very small voltage signals produced by returning echos. Some ultrasound applications also require generating a specific transmit waveform with very low distortion to obtain an adequate result. An ultrasound transceiver is described that overcomes most of the deficiencies of conventional ultrasound transceivers, with the ability to transmit high power and high frequency arbitrary waveforms with low distortion, and with the ability to monitor the transmit signal through the receiver during the transmit period.

Improved Transceiver Design

Figure 2:
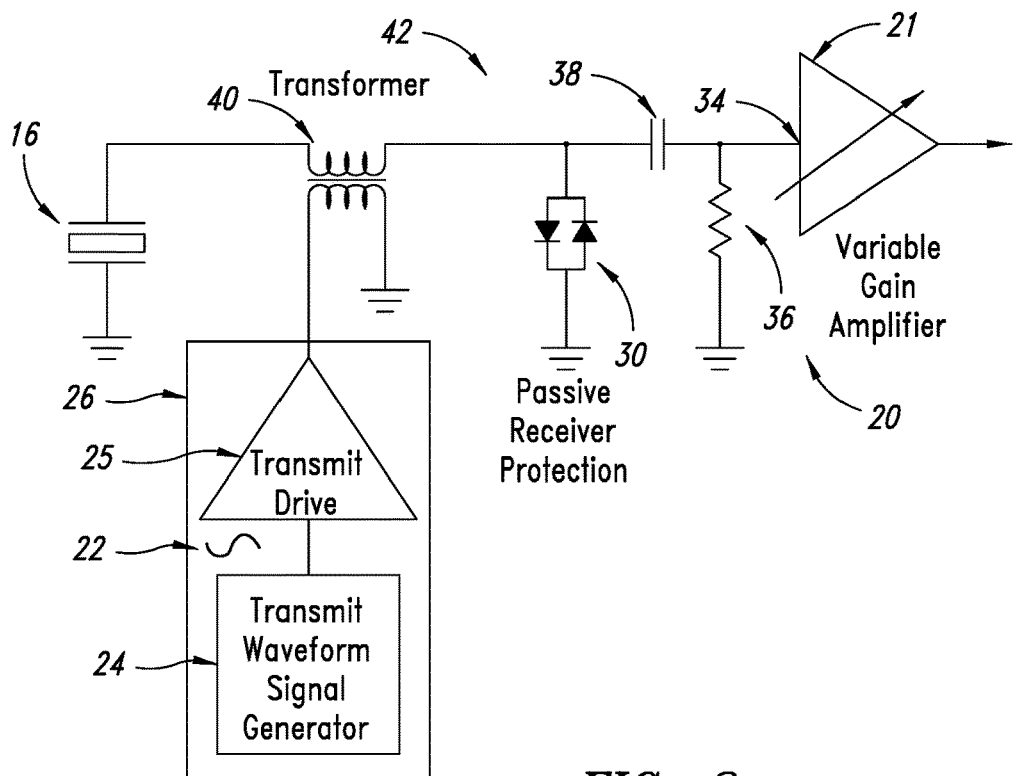
FIG. 2 is a schematic illustration of an ultrasound transceiver with a transmit/receive (T/R) circuit that replaces the T/R switch with a transformer in accordance with the present disclosure.

Elimination of T/R Switch—One improvement that can be made to the conventional transceiver design is to eliminate the T/R switch altogether. This can be accomplished with a transformer 40 that couples the transmit waveform into the receive path, as shown in the transceiver circuit 42 of FIG. 2. During a transmit, the high voltage transmit waveform 42 (with peak-to-peak voltages over 100 volts) causes the back-to-back diodes 30 to conduct, which protects the receiver circuit 20 at its input 34 by effectively grounding the input signal. The input signal is not completely grounded, as there is the approximately +/−0.8 voltage drop across the back-to-back diodes 30, but this is generally small enough to not damage the receiver circuit 20 and has a minimal effect on the transmit waveform. On receiving an echo signal from the medium by the transducer element 16, the transmit drive signal from the transmitter circuit 26 is at zero, and the transformer 40 becomes a short circuit. The received echo signal levels at the transducer element 16 are typically below the conduction thresholds of the back-to-back diodes 30 so that the diodes are at a high impedance, allowing the received signals to flow through to the input 34 of the receiver circuit 20. The typical variable gain receiver circuit 20 will have maximum gains of greater than 30 dB.

The elimination of the T/R switch 12 provides several advantages. Firstly, there is no need for a transmit period, because the transmit at the transducer element 16 can occur at any time, even while the receiver circuit 26 is active or other transceivers are transmitting or receiving. This allows for an application where multiple transmits can be employed during the echo signal acquisition period from the same or different sets of transducer elements 16. Secondly, the echo signal receive period can be started before any transmits have occurred at the transducer element 16, allowing some transducer elements to be receiving signals before they have transmitted, thus effectively eliminating any dead zone in front of the transducer element 16. Thirdly, because the receiver circuit receives a very attenuated version of the transmit waveform, the transmit waveform can be monitored to detect a faulty transmitter circuit 26 or a dead transducer element 16. Moreover, the transformer 40 provides good isolation of the high voltage circuits of the transmitter circuit 26 from the transducer element 16, which is often in close contact with living subjects. A fault in the transmitter circuit 26 is therefore prevented from becoming a shock hazard for the subject being scanned.

Figure 3:
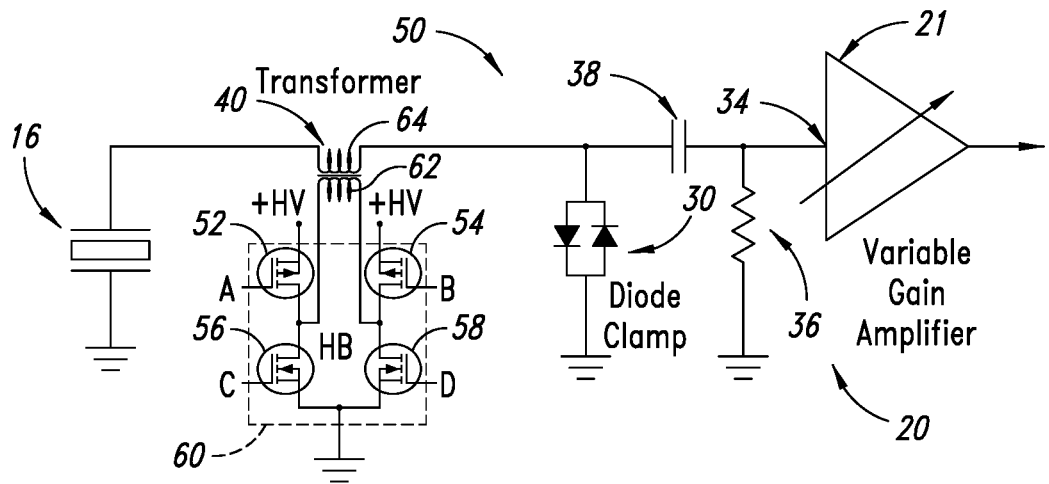
FIG. 3 is a schematic illustration of the ultrasound transcevier of FIG. 2 with the T/R circuit utilizing an H-bridge circuit in accordance with the present disclosure.

H-Bridge Transmit Generator—A further improved transceiver circuit 50 is shown in FIG. 3. The typical transmit waveform generator or transmitter circuit 26 in FIG. 1 for generating arbitrary acoustic waveforms consists of the digital waveform signal generator 24, followed by a digital-to-analog converter (not shown), followed by a power amplifier 25. It is difficult to generate high power levels with this approach because the power amplifier 25 consumes a fair amount of electrical power that is radiated away as heat. An ultrasound system with a large number of transmit channels with their own transmitter circuit 26 will be limited in transmit power by the ability to cool the circuitry.

As shown in FIG. 3, the transformer isolation of the "no T/R switch" design allows employing high voltage Field Effect Transistor (FET) switches 52, 54, 56, 58 to generate the transmit waveform, rather than expensive high power linear amplifiers. The switches 52, 54, 56, 58 are arranged in an H-Bridge circuit 60, and each of the switches 52, 54, 56, 58 is independently controlled so that the voltage driven to the transducer element 16 can be one of three levels: +HV, 0, or −HV. These levels can be derived from a single HV supply of 100 volts or greater, which facilitates waveform symmetry between positive and negative outputs—an important characteristic needed to minimize even harmonic distortion. The H-Bridge circuit 60 also allows the zero state to be actively driven, which dampens transducer element 16 ringing and improves channel-to-channel uniformity. The actively driven zero state is also critical for generating accurate arbitrary acoustic waveforms from the tri-state transmitter (H-Bridge circuit) 60.

The FETs 52, 54, 56, 58 are driven by digital signals A, B, C, D (e.g., see FIG. 3 and FIG. 6) that control the transmitter circuit output state. The digital control signals can easily be generated by a programmable logic device or by digital values read from a storage device. These devices are readily commercially available and will not be described or illustrated in detail herein. The digital signals can program transitions to new output states that are timed by a high frequency clock, typically in the range of 250-500 MHz.

Figure 6:
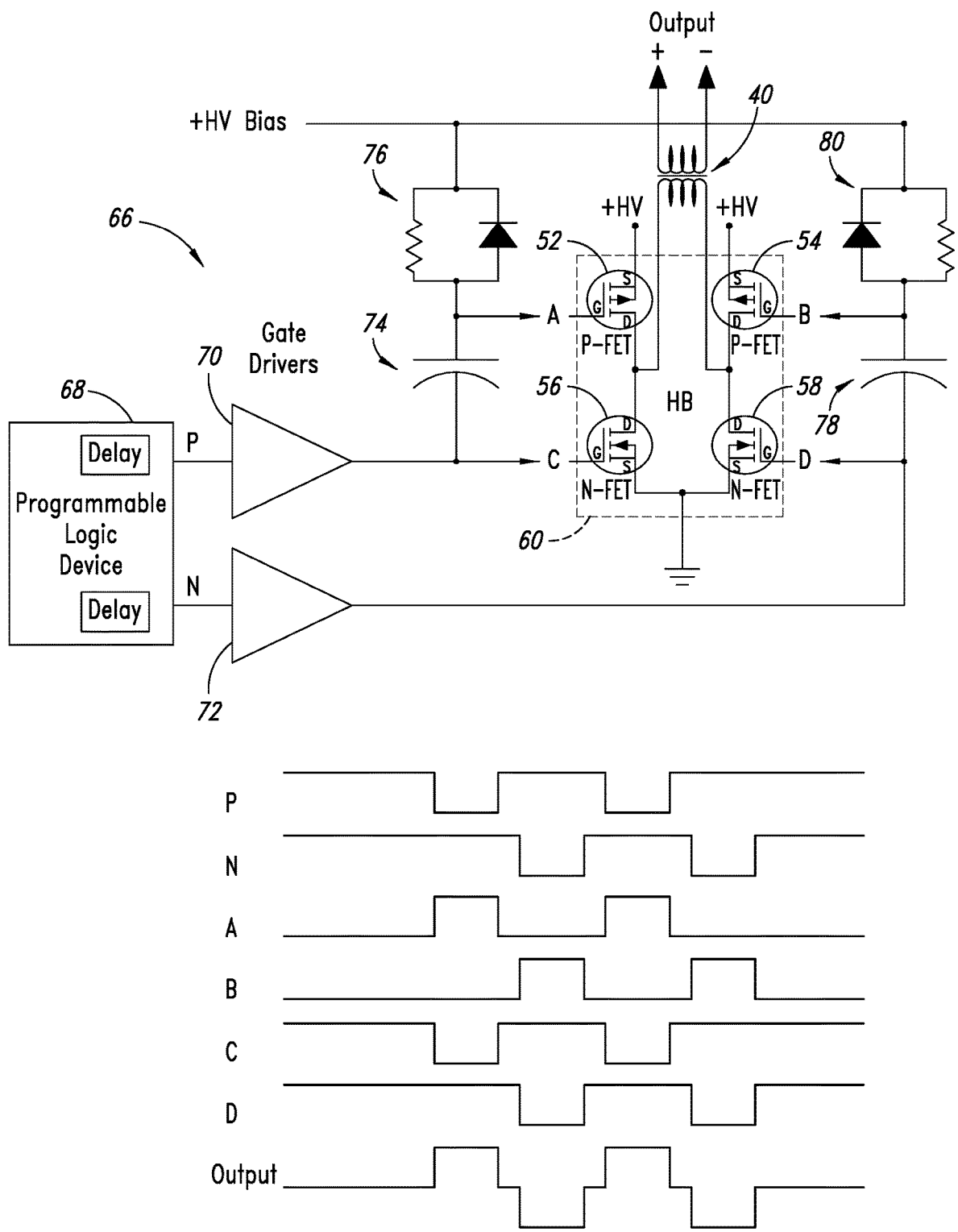
FIG. 6 is a schematic illustration of a control circuit for the transmitter circuit with waveform plots formed in accordance with a representative implementation of the present disclosure.

For example, turning on FETs 52, 58 with control signals A and D, with FETs 54, 56 control signals B and C off, applies the high voltage, HV, across the primary winding 62 of the transformer 40 in the positive direction. Turning FETs 52, 58 control signals A and D off and control signals B and C on for FETs 54, 56 applies the high voltage across the primary winding 62 of the transformer 40 in the reverse direction, generating a negative output. Similarly, turning control signals A and B off and control signals C and D on grounds both sides of the primary winding 62 and generates a zero voltage state. Because signals A and C, and also signals B and D, are always complimentary, they can be generated by single drive signals, as shown in FIG. 6. By controlling the configuration and timing of the four H-Bridge FETs 52, 54, 56, 58 using the control signals A, B, C, D, it is possible to generate a tri-state output waveform with arbitrarily timed state transitions, which when filtered by the transducer element 16's impulse response, generates an arbitrary acoustic waveform in the medium that is acoustically coupled to the transducer element 16.

Thus, this transceiver circuit 50 is capable of generating acoustic waveforms that match those from a high power linear amplifier. (See "Method and System for Arbitrary Waveform Generation Using a Tri-State Transmit Pulser," by Flynn, J. et. al., PCT/US2014/047080). Besides being lower cost, the advantage of the tri-state approach is that it is capable of generating very high power arbitrary acoustic waveforms with low power dissipation in the transmitter circuitry itself, thereby reducing power and cooling requirements for the transmit circuitry.

Reducing Non-linear Effects and Distortion—Many ultrasound applications require high linearity in the transmit waveform and low distortion in the receiver to achieve their purpose. For example, there are ultrasound applications where the transmit waveform is encoded so as to uniquely identify its signal in a mixture of acoustic signals and noise. In order to decode the transmitter's signal in the receive signal processing, it is critical to have good linearity in both the transmitted waveform and in the signal path ahead of the receiver's input.

In the previous "no T/R switch" design of transceiver circuits 42 and 50, back-to-back diodes 30 were employed to protect the receiver circuit input 34 from large voltages and act as a path to ground for the secondary winding 64 of the transmitter transformer 40 when transmit is active. While effective at protecting the receiver circuit 20 during transmit, these back-to-back diodes 30 introduce a slight distortion in the transmit waveform and non-linear characteristics into the signal path for receiving echo signals at the transducer element 16.

Figure 4:
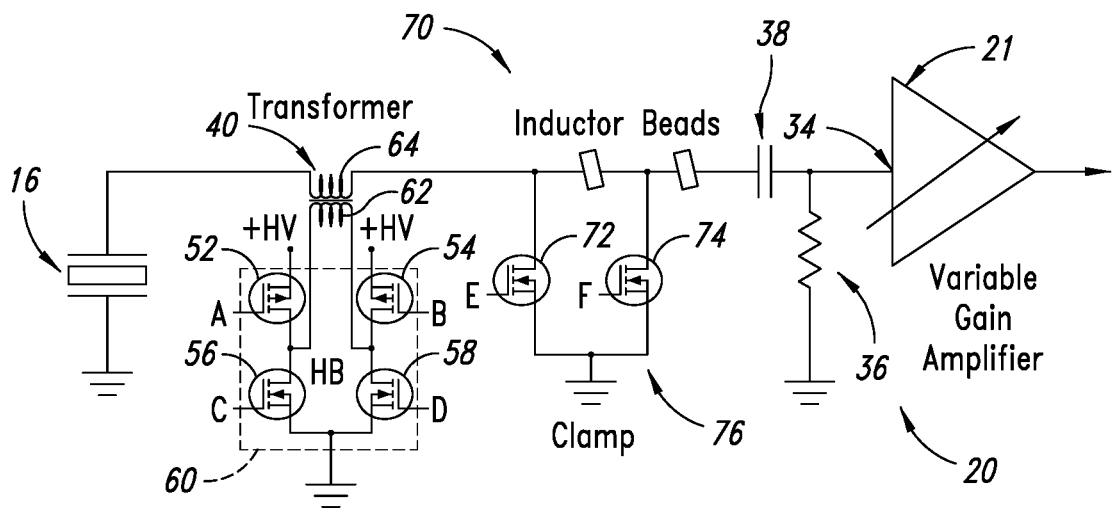
FIG. 4 is a schmatic illustration of the ultrasound transceiver circuit of FIG. 3 with the T/R circuit utilizing a clamp circuit for receiver circuit protection in accordance with the present disclosure.

To improve linearity and reduce distortion, the back-to-back diodes 30 can be replaced as shown in the transceiver circuit 70 of FIG. 4 with two parallel coupled FET switches 72, 74 that are controlled by control signals E and F, respectively, to form an active clamp circuit 76. When the FETs 72, 74 switch on, they present a very low resistance (approximately 0.1 ohms). This resistance is also fairly constant over the full output current range of the transmitter circuit 60. This active clamp circuit 76 will eliminate the crossover distortion of the passive clamp diodes 30, as well as increase receiver circuit 20 dynamic range, as the typical receiver can receive signals larger than +/−0.8 volts. With the active clamp circuit 76 providing a consistent and linear resistance, the attenuated transmit waveform signal at the input 34 of the receiver circuit 20 is an accurate representation of the transmit waveform, and can be used to monitor transmit power and duration, as well as detecting faulty transmitter circuits or transducer elements. This monitoring can be accomplished with no additional circuitry by simply capturing the receiver's non-saturated output signal during the transmit period and estimating the transmit power from the scaled down signal from the receiver. This requires knowledge of the receiver gain (during transmit) and the attenuation factor of the clamp circuit, which can be readily determined by one of skill in this technology and will not be described in detail herein.

Figure 5:
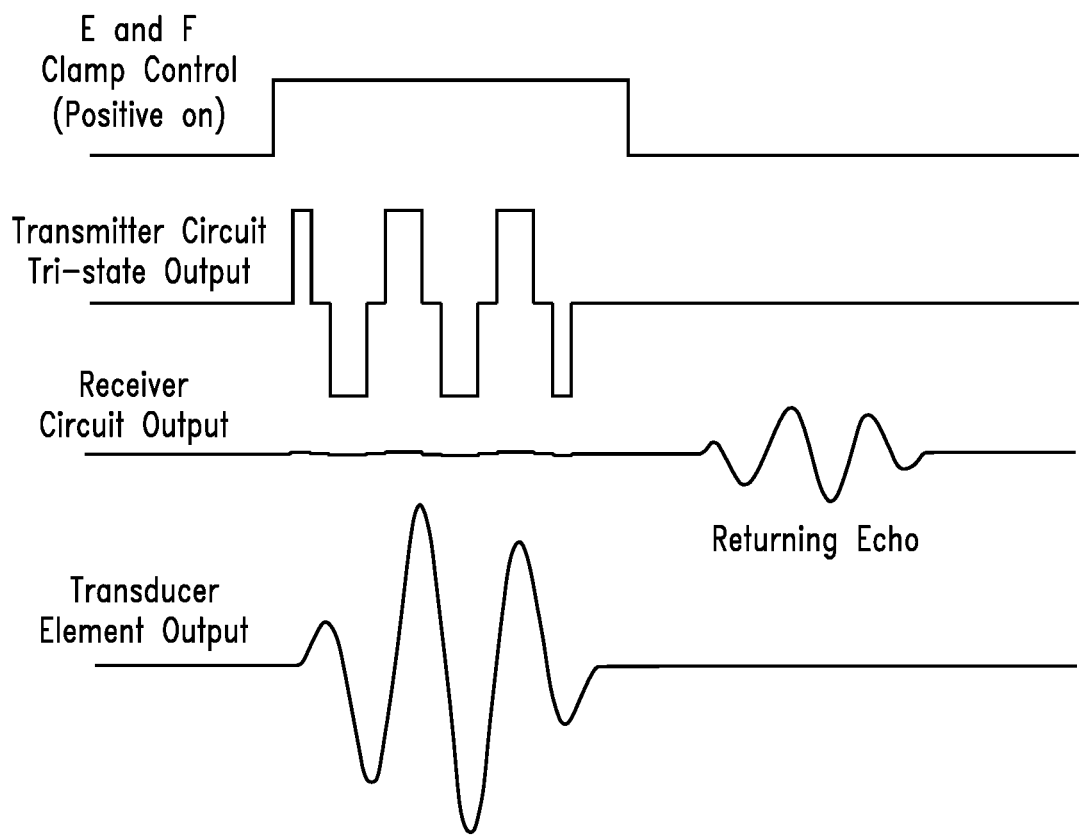
FIG. 5 is a behavioral waveform diagram of the control signal for the clamp circuit of FIG. 4 along with responsive waveform signals for components of the ultrasound transceiver circuit of FIG. 4 formed in accordance with the present disclosure.

A behavioral waveform diagram is shown in FIG. 5 for the control signal of the clamp circuit of FIG. 4 along with responsive waveform signals for components of the ultrasound transceiver circuit of FIG. 4. The control of the active clamp circuit 30 is indicated by signals E and F, which are typically switched on together. The clamp control signal is generated to correspond to the transmit duration shown in the second waveform, and it minimizes the signal level at the point of the variable gain amplifier in the receiver circuit 20. Although this adds additional complexity to the design, it can be tied to the transmit waveform duration, and generated automatically by the digital transmit signal generator circuit 60 for most waveforms. The ability to transmit at any time during the receive period is still preserved. The diagram in FIG. 5 also shows the receiver circuit 20 output in the third waveform and the transducer element 16 output in the fourth waveform. Note that there is a small signal of the receiver output during transmit, which can be used to estimate transmit power. This could be somewhat enlarged if desired.

The H-Bridge circuit 60, if not properly designed and programmed, can also be a source of distortion in the transmit waveform. The FETs 52, 54, 56, 58 do not switch instantaneously, and while one FET is turning on and another turning off, there can be transient voltage effects that compromise the waveform. These effects can be minimized by fine adjustments to the timing of the transitions. Small delays can be introduced for the control signals that can be adjusted for propagation delays and component variation. The small delays can be programmed at system startup using a calibration procedure that minimizes the distortion component.

For example, FIG. 6 illustrates a represenative control circuit 66 for the transmitter circuit 60 shown in FIG. 4. The control circuit 66 in this implementation includes a programmable logic device 68 having outputs P and N coupled to a P gate driver 70 and an N gate driver 72, respectively. The P gate driver 70 has its output forming the C digital signal coupled directly to the gate of the N-FET 56. The P gate driver 70 output is also the A digital signal that is input to the gate of the P-FET 52 through a capacitor 74. A positive +HV bias rail is connected through a parallel diode-resistor circuit 76 to the gater of the P-FET 52. Similarly, the output of the N gate driver 72 is the D digital signal coupled to the gate of the N-FET 58 and, through the capacitor 78 to the gate of the P-FET 54 as digital signal B. The +HV bias rail is also coupled to the gate of the P-FET 54 through a parallel diode-resistor circuit 80.

At the bottom of FIG. 6 is the waveform plot over time for the P and N outputs and the A, B, C, D gate signals as well as the output signal Output, that is received at the transducer element 16.

In general, in the following claims, the terms used should not be construed to limit the claims to the specific implementations disclosed in the specification and the claims, but should be construed to include all possible implementations along with the full scope of equivalents to which such claims are entitled. Accordingly, the claims are not limited by the disclosure.

The invention claimed is:

1. A circuit, comprising:
   a transducer element structured to emit an ultrasound signal and to receive a reflected ultrasound signal;
   a transformer circuit coupled to the transducer element, the transformer circuit comprising a transformer having a primary winding and a secondary winding, the secondary winding coupled to the transducer element;
   a transmit waveform circuit coupled to the primary winding of the transformer and structured to generate a transmit waveform signal to the transducer element via the transformer circuit;
   a receiver circuit having an input coupled to the secondary winding of the transformer and structured to be coupled to the transducer element.

2. The circuit of claim 1 wherein the transmit waveform circuit comprises an H-bridge circuit.

3. The circuit of claim 2 further comprising a clamp circuit coupled between the secondary winding of the transformer and the input of the receiver circuit.

4. The circuit of claim 3 wherein the clamp circuit comprises an active clamp circuit having a pair of FET switches coupled in parallel to the input of the receiver circuit.

5. The circuit of claim 4 wherein each of the FET switches in the pair of FET switches have a control terminal that is coupled to the transmit waveform generator circuit to receive an on-signal that is tied to a duration of transmit waveform signal.

6. An ultrasound device, comprising:
   a transducer circuit structured to transmit ultrasound signals and receiving corresponding echo signals and generating returning echo signals;
   a variable gain receiver having an input coupled to the transducer circuit;
   a transceiver capable of generating over 100 volts peak-to-peak waveforms across the transducer and receiving the returning echo signals from the transducer of less than one volt peak-to-peak, the transceiver including:
      a transformer having a primary winding and a secondary winding, the primary winding coupled to the transducer;
      a transmitter circuit coupled through the transformer to the transducer, the transmitter circuit comprising a transmit waveform generator structured to generate a transmit waveform, the transmit waveform generator coupled to the primary winding of the transformer so that the primary winding is driven by the transmit waveform generator, and the secondary is connected on one side to the transducer circuit and on another other side to the input of the variable gain receiver, with a maximum gain of at least 30 dB; and
      a protection circuit coupled between the secondary winding of the transformer and the input of the variable gain receiver and structured such that when the protection circuit is active it provides an impedance in the range of 0.1 to 1.0 ohms from the input of the variable gain receiver to ground during a transmit period of the transceiver so that the input of the variable gain receiver provides an effective ground for the transformer secondary winding during the transmit period; wherein
   the variable gain receiver can be active during the transmit period and can amplify a small voltage across the protection circuit to monitor the transmit waveform for amplitude and duration.

7. The ultrasound device of claim 6, where the impedance of the protection circuit when active is resistive and constant over a current range of the transmitter circuit output.

8. The ultrasound device of claim 6, where the activation of the protection circuit on the input of the variable gain receiver is automatically performed based on a duration of the transmit waveform.

9. The ultrasound device of claim 6, where the transmitter circuit can be activated multiple times during a receive period, with concurrent active control of the receiver input clamp, so that the receiver is minimally affected during each activation.

10. The ultrasound device of claim 6 where the transmit waveform generator is structured to produce a tri-state output waveform that comprises the states of −HV, zero, and +HV, where HV can be set over a range from less than 2 volts to greater than 100 volts.

11. The ultrasound device of claim 10, where the three states of the tri-state output waveform are generated from four FETs that are configured in an H-Bridge circuit and, and each of the four FETs are structured to be switched on and off independently.

12. The ultrasound device of claim 11, where a duration of each state in the tri-state output waveform can be programmed to generate a tri-level output waveform that when filtered by the transducer's impulse response produces a desired arbitrary acoustic output waveform.

13. The ultrasound device of claim 11, wherein a timing of a switching on and off of each of the FETs can be adjusted with small delays to minimize distortion in an output of the transmitter circuit.

\* \* \* \* \*